(12) United States Patent
Takei et al.

(10) Patent No.: US 12,080,103 B2
(45) Date of Patent: Sep. 3, 2024

(54) EYEBALL DETECTION DEVICE, EYE-GAZE TRACKING DEVICE, EYEBALL DETECTION METHOD, AND MEDIUM

(71) Applicant: JVCKENWOOD Corporation, Yokohama (JP)

(72) Inventors: Hiroyuki Takei, Yokohama (JP); Shuji Hakoshima, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 387 days.

(21) Appl. No.: 17/543,848

(22) Filed: Dec. 7, 2021

(65) Prior Publication Data

US 2022/0092880 A1    Mar. 24, 2022

Related U.S. Application Data

(63) Continuation of application No. PCT/JP2020/024727, filed on Jun. 24, 2020.

(30) Foreign Application Priority Data

Jul. 19, 2019    (JP) .................................. 2019-133582

(51) Int. Cl.
*G06V 40/18*      (2022.01)
*G06T 7/20*       (2017.01)
(Continued)

(52) U.S. Cl.
CPC ................. *G06V 40/18* (2022.01); *G06T 7/20* (2013.01); *G06T 7/50* (2017.01); *G06T 7/70* (2017.01);
(Continued)

(58) Field of Classification Search
CPC .... G06V 40/18; G06V 40/161; G06V 10/768; G06V 40/193; G06V 40/165; G06T 7/20;
(Continued)

(56) References Cited

U.S. PATENT DOCUMENTS

2016/0142673 A1*   5/2016  Rao ..................... G06V 40/193
                                                      348/14.08

FOREIGN PATENT DOCUMENTS

JP          2008-125619         6/2008

OTHER PUBLICATIONS

Peter et al, ("Localizing Parts of Faces Using a Consensus of Exemplars", IEEE Transactions of Pattern Analysis and Machine Intelligence, vol. 35, No. 12, Dec. 2013, pp. 2930-2940) (Year: 2013).*

(Continued)

*Primary Examiner* — Amara Abdi
(74) *Attorney, Agent, or Firm* — Amin, Turocy & Watson, LLP

(57) ABSTRACT

An eyeball detection device includes an imaging device that obtains a face image which includes the left and right eyeball images of the target person; a first distance calculating unit that calculates a first-type distance representing the distance between the target person and the imaging device; and an eyeball searching unit that performs a search for the left and right eyeball images from the face image and, when only one of the left and right eyeball images of the target person is detected, searches for the other eyeball image of the target person based on the search result regarding the already-detected eyeball image as obtained by the eyeball detecting unit, based on the first-type distance, and based on a second-type distance representing the distance between the left and right eyeballs of the target person.

6 Claims, 7 Drawing Sheets

(51) Int. Cl.
    *G06T 7/50*     (2017.01)
    *G06T 7/70*     (2017.01)
    *G06V 40/16*     (2022.01)

(52) U.S. Cl.
    CPC .. *G06V 40/161* (2022.01); *G06T 2207/30201* (2013.01)

(58) Field of Classification Search
    CPC ... G06T 7/50; G06T 7/70; G06T 2207/30201; G06T 2207/10012; G06T 7/73; A61B 3/113; A61B 3/0025
    See application file for complete search history.

(56) References Cited

OTHER PUBLICATIONS

International Search Report and Written Opinion for International Application No. PCT/JP2020/024727 mailed on Sep. 15, 2020 9 pages.
Extended European Search Report for European Patent Application No. 20842949.8 dated Jun. 28, 2022.
Belhumeur, et al. "Localizing Parts of Faces Using a Consensus of Exemplars", IEEE Transactions on Pattern Analysis and Machine Intelligence, vol. 35, No. 12, Dec. 1, 2013, pp. 2930-2940.

* cited by examiner

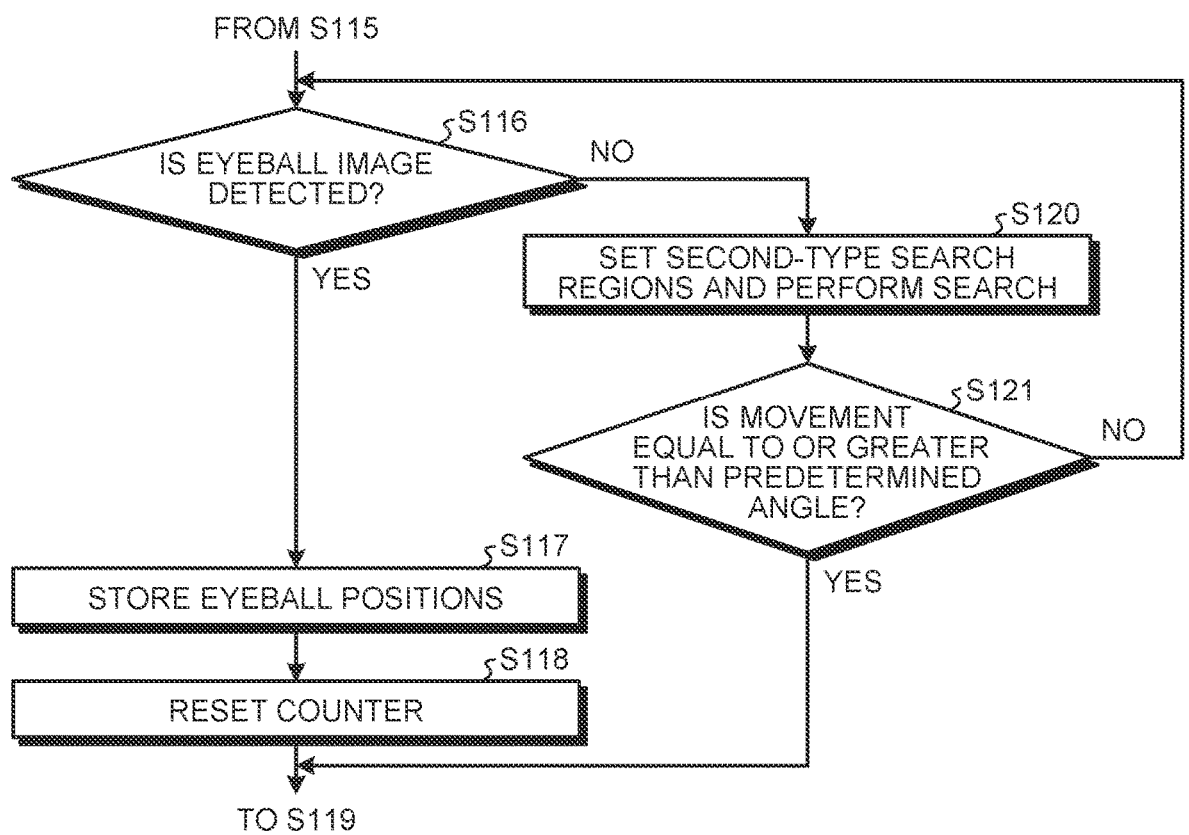

EYEBALL DETECTION DEVICE, EYE-GAZE TRACKING DEVICE, EYEBALL DETECTION METHOD, AND MEDIUM

CROSS-REFERENCE TO RELATED APPLICATION(S)

This application is a Continuation of PCT international application Ser. No. PCT/JP2020/024727 filed on Jun. 24, 2020 which designates the United States, incorporated herein by reference, and which claims the benefit of priority from Japanese Patent Application No. 2019-133582, filed on Jul. 19, 2019, incorporated herein by reference.

BACKGROUND

1. Technical Field

The present disclosure is related to an eyeball detection device, an eye-gaze tracking device, an eyeball detection method, and medium.

2. Description of the Related Art

As an eye-gaze tracking device that tracks the eye gaze of a subject, a configuration is known in which the face of the subject is captured using, for example, a camera; left and right eyeball images are detected by searching the captured face image; and the eye gaze of the subject is tracked based on the detection result (for example, refer to Japanese Patent Application Laid-open No. 2008-125619 A).

In the eye-gaze tracking device disclosed in Japanese Patent Application Laid-open No. 2008-125619 A, for example, even if one of the left and right eyeball images is lost, it is necessary to search for both of the left and right eyeball images from the face image, which requires a long processing time. Moreover, the same issue is faced also in other types of devices, such as a face recognition device, in which eyeball images are searched from the face image.

SUMMARY

It is an object of the present disclosure to at least partially solve the problems in the conventional technology.

An eyeball detection device according to the present disclosure comprising: an imaging device that obtains a face image which includes left and right eyeball images of target person; a first distance calculating unit that calculates a first-type distance representing distance between the target person and the imaging device; and an eyeball searching unit that performs a search for the left and right eyeball images from the face image and, when one eyeball image of the left and right eyeball images of the target person is detected, searches for other eyeball image of the target person from the face image based on search result regarding the one eyeball image as obtained by the eyeball detecting unit, based on the first-type distance, and based on a second-type distance representing distance between left and right eyeballs of the target person.

An eye-gaze tracking device according to the present disclosure that detects left and right eyeball images of target person using the eyeball detection device above, and tracks eye gaze of the target person based on detection result.

An eyeball detection method according to the present disclosure comprising: obtaining a face image that includes left and right eyeball images of target person; calculating a first-type distance representing distance between the target person and the imaging device; performing a search for the left and right eyeball images from the face image; and searching that, when one eyeball image of the left and right eyeball images of the target person is detected, includes searching for other eyeball image of the target person from the face image based on search result regarding the one eyeball image, based on the first-type distance, and based on a second-type distance representing distance between left and right eyeballs of the target person.

A non-transitory computer readable recording medium storing therein an eyeball detection program that causes a computer to execute: an operation of obtaining a face image that includes left and right eyeball images of target person; an operation of calculating a first-type distance representing distance between the target person and the imaging device; an operation of performing a search for the left and right eyeball images from the face image; and an operation of searching that, when one eyeball image of the left and right eyeball images of the target person is detected, includes searching for other eyeball image of the target person from the face image based on search result regarding the one eyeball image, based on the first-type distance, and based on a second-type distance representing distance between left and right eyeballs of the target person.

BRIEF DESCRIPTION OF THE DRAWINGS

FIG. 9 is a flowchart for explaining another example of the eyeball detection method according to the present embodiment.

DETAILED DESCRIPTION OF THE PREFERRED EMBODIMENTS

An exemplary embodiment of an eyeball detection device, an eye-gaze tracking device, an eyeball detection method, and an eyeball detection program according to the present disclosure is described below with reference to the accompanying drawings. However, the present disclosure is not limited by the embodiment described below. Moreover, the constituent elements explained in the embodiment include the constituent elements that are simple and replaceable by a person skilled in the art, or include practically identical constituent elements.

The following explanation is given about the positional relationship of different parts by setting a three-dimensional global coordinate system. The direction parallel to a first axis in a predetermined plane is treated as the X-axis direction; the direction parallel to a second axis in the predetermined plane, which is orthogonal to the first axis, is treated as the Y-axis direction; and the direction parallel to a third axis, which is orthogonal to the first and second axes, is treated as the Z-axis direction. The predetermined plane includes the XY plane.

[Eye-Gaze Tracking Device]

Figure 1:
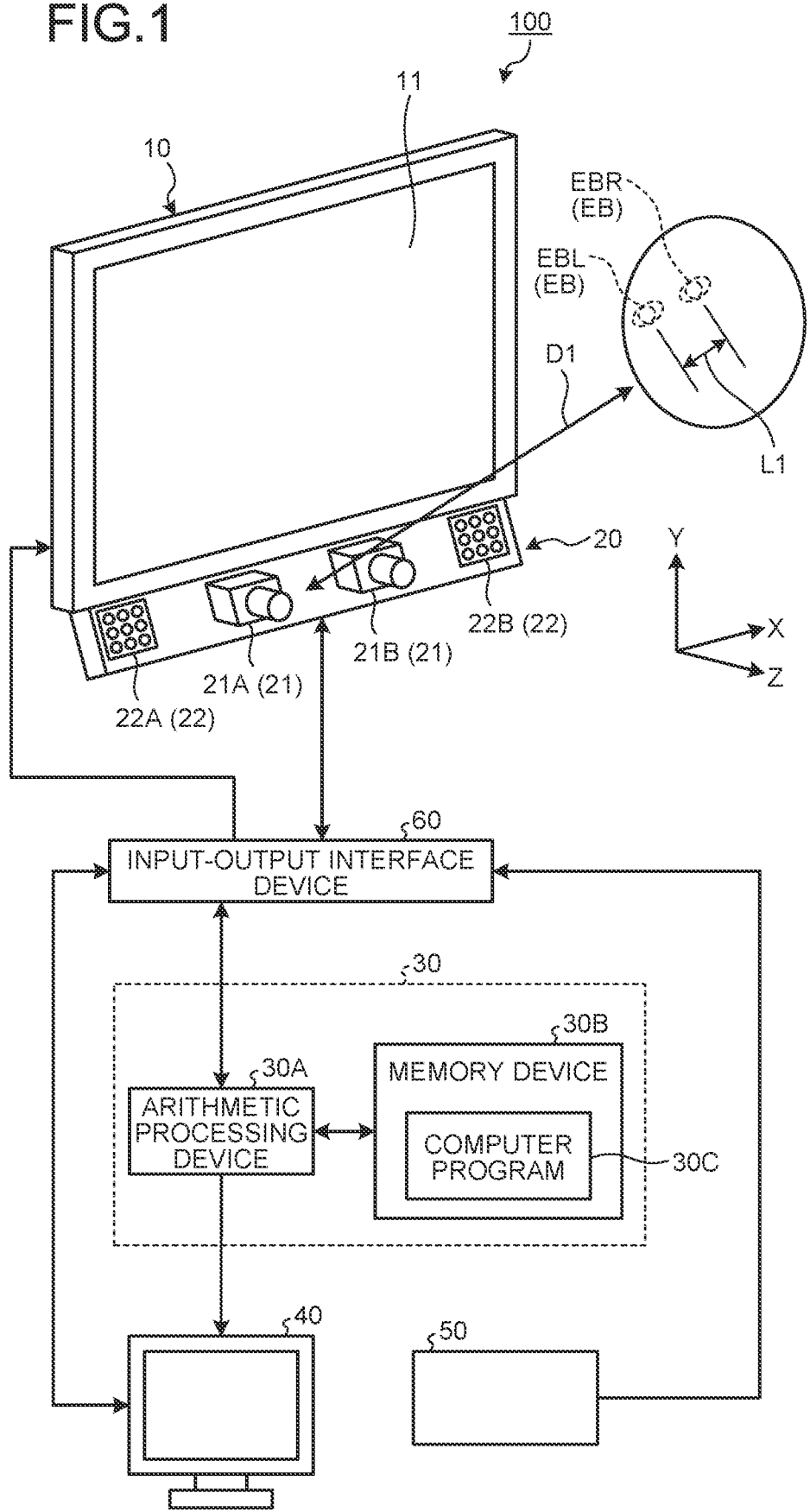
FIG. 1 is a diagram that schematically illustrates an example of an eye-gaze tracking device according to an embodiment.

FIG. 1 is a diagram that schematically illustrates an example of an eye-gaze tracking device (an eyeball detection device) 100 according to the present embodiment. The eye-gaze tracking device 100 according to the present embodiment tracks the eye gaze of the subject (target person). As far as the eye-gaze tracking device 100 is concerned, it is possible to use various types of devices capable of tracking the eye gaze of the subject, such as a device that tracks the eye gaze based on, for example, the positions of the pupils of the eyes of the subject and based on the position of the corneal reflect image of the subject; or a device that tracks the eye-gaze based on the positions of the inner corners of the eyes of the subject and based on the positions of the irises of the subject.

As illustrated in FIG. 1, the eye-gaze tracking device 100 includes a display device 10, an image obtaining device 20, a computer system 30, an output device 40, an input device 50, and an input-output interface device 60. The display device 10, the image obtaining device 20, the computer system 30, the output device 40, and the input device 50 perform data communication via the input-output interface device 60. The display device 10 as well as the image obtaining device 20 includes a driving circuit (not illustrated).

The display device 10 includes a flat panel display such as a liquid crystal display (LCD) or an organic electroluminescence display (OLED). In the present embodiment, the display device 10 includes a display unit 11. The display unit 11 displays information such as images. Moreover, the display unit 11 is positioned to be practically parallel to the XY plane. The X-axis direction represents the horizontal direction of the display unit 11; the Y-axis direction represents the vertical direction of the display unit 11; and the Z-axis direction represents the depth direction orthogonal to the display unit 11. The display device 10 can alternatively be a head-mounted display. In the case of a head-mounted display, a configuration such as the image obtaining device 20 is installed inside a head-mounted module.

The image obtaining device 20 obtains image data of a face image that includes left and right eyeballs EB (a left eyeball EBL and a right eyeball EBR) of the subject, and sends the obtained image data to the computer system 30. The image obtaining device 20 includes an imaging device 21. The imaging device 21 obtains image data by capturing the face portion including the left and right eyeballs EB of the subject. The imaging device 21 includes various types of cameras according to the method to be implemented for tracking the eye gaze of the subject. For example, in the case of implementing the method in which the eye gaze is tracked based on, for example, the positions of the pupils of the eyes of the subject and the positions of the corneal reflex images of the subject; the imaging device 21 includes an infrared camera, as well as includes an optical system capable of transmitting near-infrared light having the wavelength of, for example, 850 [nm] and an imaging device capable of receiving near-infrared light. Alternatively, in the case of implementing the method in which the eye gaze is tracked based on, for example, the positions of the inner corners of the eyes of the subject and based on the positions of the irises of the subject; the imaging device 21 includes a visible light camera. Meanwhile, the imaging device 21 outputs frame synchronization signals. The period of the frame synchronization signals can be set to, for example, 20 [msec]. However, that is not the only possible case. Moreover, the imaging device 21 is capable of detecting a first-type distance D between the imaging device 21 and the face of the subject. Hence, the imaging device 21 can be configured as, for example, a stereo camera including a first camera 21A and a second camera 21B. However, that is not the only possible example.

Meanwhile, in the case of implementing the method in which the eye gaze is tracked based on, for example, the positions of the pupils of the eyes of the subject and the positions of the corneal reflex images of the subject, the image obtaining device 20 includes an illumination device 22 that illuminates the eyeballs EB of the subject. The illumination device 22 includes an LED light source (LED stands for light emitting diode) and is capable of emitting near-infrared light having the wavelength of, for example, 850 [nm]. However, in the case of implementing the method in which the eye gaze is tracked based on, for example, the positions of the inner corners of the eyes of the subject and based on the positions of the irises of the subject, the illumination device 22 need not be installed. The illumination device 22 emits a detection light in synchronization with the frame synchronization signals output by the imaging device 21. The illumination device 22 can be configured to include, for example, a first light source 22A and a second light source 22B. However, that is not the only possible case.

The computer system 30 comprehensively controls the operations of the eye-gaze tracking device 100. The computer system 30 includes an arithmetic processing device 30A and a memory device 30B. The arithmetic processing device 30A includes a microprocessor such as a CPU (central processing unit). The memory device 30B includes memories such as a ROM (read only memory) and a RAM (random access memory) or includes a storage device. The arithmetic processing device 30A performs arithmetic processing according to a computer program 30C that is stored in the memory device 30B.

The output device 40 includes a display device such as a flat panel display. Moreover, the output device 40 can also include a printing device. The input device 50 generates input data in response to being operated. The input device 50 includes a keyboard or a mouse for a computer system. Moreover, the input device 50 can also include a touch sensor installed in the display unit of the output device 40 that is a display device.

In the eye-gaze tracking device 100 according to the present embodiment, the display device 10 and the computer system 30 are separate devices. Alternatively, the display device 10 and the computer system 30 can be integrated. For example, the eye-gaze tracking device 100 can include a tablet personal computer. In that case, the tablet personal computer can be equipped with a display device, an image obtaining device, a computer system, an input device, an output device, and the like.

Figure 2:
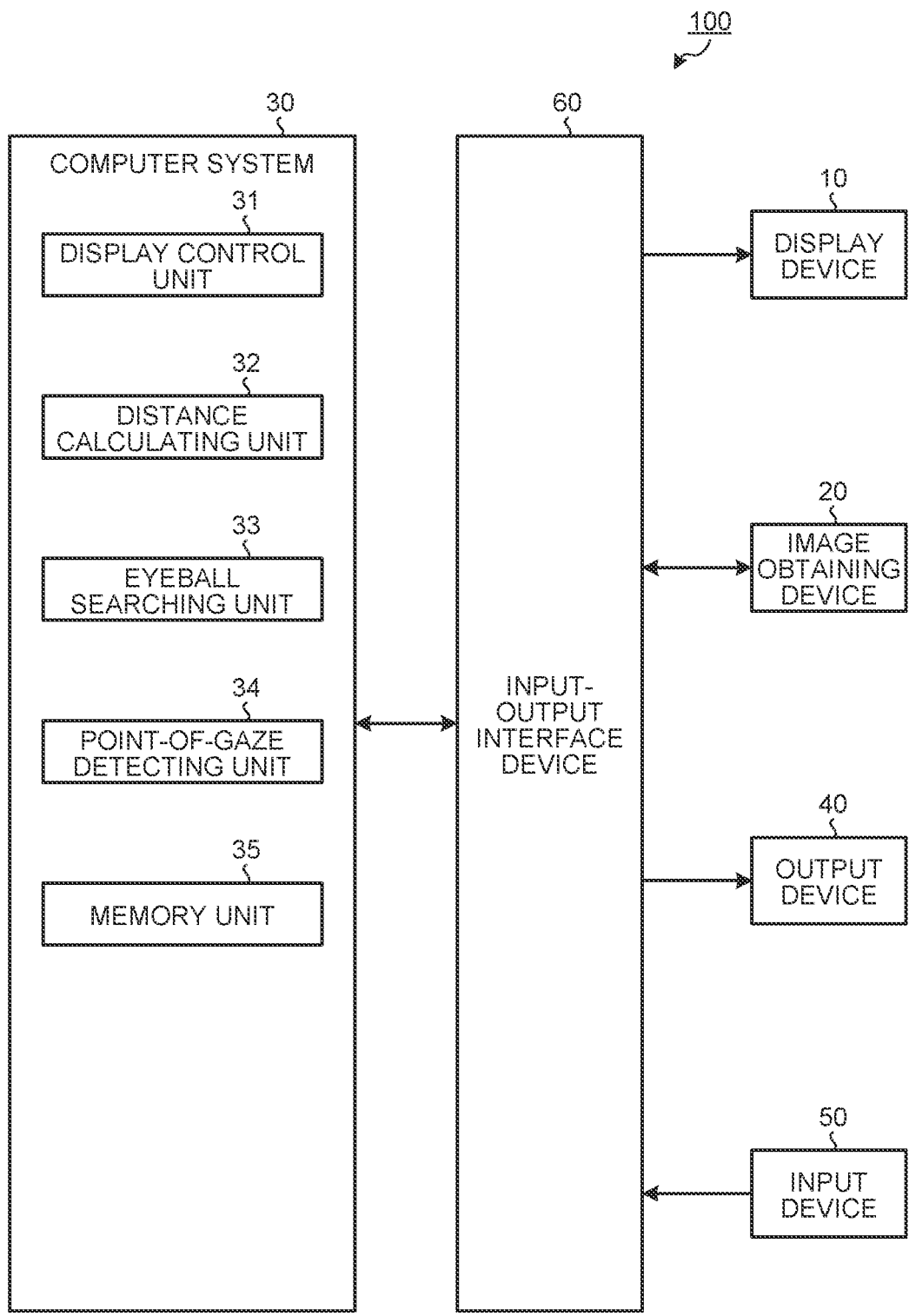
FIG. 2 is a functional block diagram illustrating an example of the eye-gaze tracking device.

FIG. 2 is a functional block diagram illustrating an example of the eye-gaze tracking device 100. As illustrated in FIG. 2, the computer system 30 includes a display control unit 31, a distance calculating unit (a first distance calculating unit, a second distance calculating unit) 32, an eyeball searching unit 33, a point-of-gaze detecting unit 34, and a memory unit 35. The functions of the computer system 30 are implemented using the arithmetic processing device 30A and the memory device 30B (see FIG. 1). Meanwhile, some of the functions of the computer system 30 can be implemented on the outside of the eye-gaze tracking device 100.

In the display unit 11, the display control unit 31 displays, for example, images, videos, and characters at which the subject is to be made to gaze.

The distance calculating unit 32 calculates a subject-device distance (the first-type distance) D1 and an interocular distance (a second-type distance) L1. The subject-device distance D1 is the distance between the target person and the imaging device 21. The interocular distance L1 is the distance between the left eyeball EBL and the right eyeball EBR of the target person. The distance calculating unit 32 calculates the subject-device distance D1 from the images captured by the first camera 21A and the second camera 21B of the imaging device 21.

The interocular distance L1 can be measured in advance, and the measurement result can be stored in the memory unit 35. In that case, the distance calculating unit 32 can obtain the measurement result, which is stored in the memory unit 35, as the interocular distance L1.

Even if the measurement result of the interocular distance L1 is not obtained in advance, the distance calculating unit 32 can obtain the interocular distance L1 according to the following sequence when the left and right eyeball images are detected in the face image captured by the imaging device 21. That is, if S [mm] represents the size of the subject image formed in the photodetection region of the imaging device 21 and if F [mm] represents the focal length of the lens, then an actual size R [mm] of the photographic subject present at the distance D [mm] from the imaging device 21 can be obtained using [Expression 1] given below.

$$R = \frac{D \times S}{F} \quad (1)$$

Moreover, if P[μm/px] represents the pixel pitch of the light receiving unit of the imaging device 21, then a distance L[px] between two points in the image captured by the imaging device 21 can be obtained using [Expression 2] given below.

$$L = \frac{S}{P} \times 1000 \quad (2)$$

Thus, if D1 represents the distance between the subject and the imaging device 21 (i.e., the subject-device distance) and if L2 represents the distance between the two eyeball images in the face image captured by the imaging device 21 (hereinafter, referred to as an inter-eyeball-image distance), then the interocular distance L1 [mm] representing the actual distance between the left and right eyeballs of the subject can be obtained using [Expression 3] based on [Expression 1] and [Expression 2].

$$L1 = \frac{D1 \times P \times L2}{F \times 1000} \quad (3)$$

Using [Expression 3] given above, the distance calculating unit 32 can obtain the interocular distance L1 based on the subject-device distance D1 and the inter-eyeball-image distance L2.

The eyeball searching unit 33 searches for left and right eyeball images E (i.e., eyeball images EL and ER) from the face image obtained by the imaging device 21. For example, the eyeball searching unit 33 compares the face image with eyeball patterns stored in advance in the memory unit 35, and searches for the eyeball images E based on the comparison result. As far as the search period is concerned, the eyeball searching unit 33 can set a period same as, for example, the period of the frame synchronization signals (for example, 20 [msec]) that are output from the imaging device 21.

For example, in the initial search, the eyeball searching unit 33 searches for the eyeball images E across the entire face image and, if the eyeball images E are detected, stores the eyeball positions based on the eyeball images E in the memory unit 35. Examples of the eyeball positions include the reference coordinates, the pupil coordinates, and the corneal reflex coordinates. The reference coordinates represent the coordinates of the reference positions for the eyeball images E, such as the coordinates of the center positions of the eyeball images E. The pupil coordinates represent the coordinates indicating the positions of the pupil centers in the eyeball images E. The corneal reflex coordinates represent the coordinates of the positions of the corneal reflex centers in the eyeball images E. Meanwhile, the pupil coordinates or the corneal reflex coordinates can also be treated as the reference coordinates. In the search from the second time onward, the eyeball searching unit 33 searches for the regions within a predetermined radius around the eyeball positions stored in the memory unit 35. As a result, the processing time gets shortened as compared to the case in which the entire face image is searched every time.

The point-of-gaze detecting unit 34 detects position data of the point of gaze of the subject. In the present embodiment, based on the left and right eyeball images present in the face image of the subject captured by the imaging device 21, the point-of-gaze detecting unit 34 detects the eye-gaze vector of the subject as defined in the three-dimensional global coordinate system. Moreover, the point-of-gaze detecting unit 34 detects, as the position data of the point of gaze of the subject, position data of the point of intersection between the detected eye-gaze vector of the subject and the display unit 11 of the display device 10. That is, in the present embodiment, the position data of the point of gaze represents the position data of the point of intersection between the eye-gaze vector of the subject as defined in the three-dimensional global coordinate system and the display unit 11 of the display device 10. As a result, it becomes possible to detect that position in the display unit 11 at which the subject is gazing. The point-of-gaze detecting unit 34 detects the position data of the point of gaze of the subject in each specified sampling period. The sampling period can be set to be same as, for example, the period of the frame synchronization signals (for example, 20 [msec]) that are output from the imaging device 21.

The memory unit 35 is used to store the distance data of the subject-device distance D1 and the interocular distance L1, the distance data of the inter-eyeball-image distance L2, the position data of the eyeball images, point-of-gaze data, and the like. The memory unit 35 is used to store an eyeball detection program that causes a computer to perform the following operations: an operation of obtaining a face image including the left and right eyeball images of the subject; an operation of calculating the subject-device distance D1; an operation of searching for the eyeball images from the face image; and, when only one of the left and right eyeball images of the subject is detected as a result of the search, an operation of searching the other eyeball image of the subject from the face image based on the search result regarding the detected eyeball image, based on the subject-device distance D1, and based on the interocular distance L1 of the subject.

[Eyeball Detection Method]

Given below is the explanation of an eyeball detection method according to the present embodiment. At the time of detecting the eye gaze of the subject using the eye-gaze tracking device 100, the eyeball detection method according to the present embodiment can be implemented for detecting the eyeballs of the subject.

Figure 3:
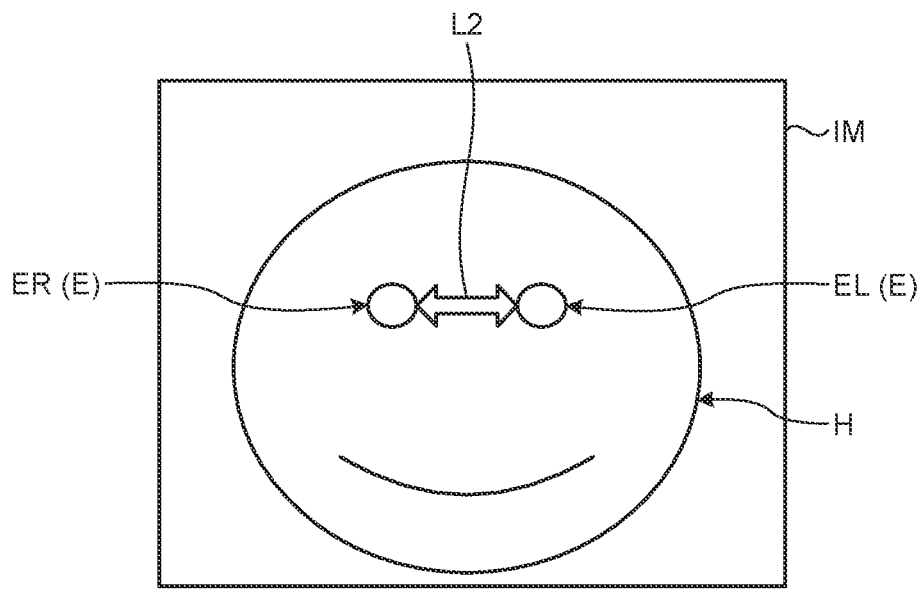
FIG. 3 is a diagram illustrating an example of a face image of a subject as obtained by an imaging device.

FIG. 3 is a diagram illustrating an example of a face image of a subject as obtained by the imaging device 21. As illustrated in FIG. 3, the eyeball searching unit 33 searches for the eyeball images E of a subject H from a face image IM obtained by the imaging device 21. With reference to FIG. 3, the eyeball searching unit 33 can compare the face image IM with eyeball image patterns stored in advance in the memory unit 35, and can detect the left eyeball image EL and the right eyeball image ER as the eyeball images E. If the eyeball images E indicating the left eyeball image EL and the right eyeball image ER are successfully detected, then the distance calculating unit 32 calculates the inter-eyeball-image distance L2 between the left and right eyeball images E; calculates the interocular distance L1 based on that calculation result and [Expression 3] given earlier; and stores the interocular distance L1 in the memory unit 35. Moreover, based on the detection result, the eyeball searching unit 33 calculates the positions of the left and right eyeball images EL in the face image IM, and stores the calculation result in the memory unit 35.

The point-of-gaze detecting unit 34 detects the eye-gaze vector of the subject based on the left and right eyeball images E present in the face image IM. Then, after each predetermined sampling period, the point-of-gaze detecting unit 34 detects, as the position data of the point of gaze of the subject, the position data of the point of intersection between the detected eye-gaze vector of the subject and the display unit 11 of the display device 10.

There are times when the eyeball searching unit 33 fails to detect the eyeball images E in a particular instance of the search. As far as the factors resulting in a failure in the detection of the eyeball images E are concerned; firstly, it is possible to think of blinking performed by the subject. Because of the blinking performed by the subject, the face image IM is obtained in which the eyelids are closed. Hence, the eyeball searching unit 33 cannot detect, from the face image IM, the eyeball images E that correspond to the eyeball patterns stored in advance. However, in the case of blinking, although the eyelids are closed, the positions of the left eyeball image EL and the right eyeball images ER almost remain the same. Besides, the duration for which the eyelids are closed is short. For that reason, if blinking is the factor resulting in a failure in the detection of the eyeball images E, even if the subject has closed the eyelids in a particular instance of the search, it is highly likely that the subject has the eyelids opened in the following instances of the search. Hence, when blinking is the factor, in the following instances of the search, the search is performed over the same search range as the search range in the previous instance of the search, and it is highly likely that the eyeball images E are detected. Thus, when the detection of the eyeball images E is not successful; in the next instance of the search, the eyeball searching unit 33 performs the search over the same search range as the search range in the previous instance of the search.

As another example of not being able to detect the eyeball images E, it is possible to think of the case in which the position of the face of the subject changes due to turning the face away or due to lowering the eyes. Accompanying the change in the position of the face, the positions of the left and right eyeballs EB are likely to move, and the period of time for which the eyeball images E cannot be detected becomes longer than in the case of blinking. Hence, when a change in the position of the face is the factor for not being able to detect the eyeball images E, it becomes necessary to again perform a search for the eyeball images E from the face image. Thus, if the failure in the detection in the eyeball images E continues for, for example, a predetermined period of time or beyond, then the eyeball searching unit 33 changes the search method in the following manner.

Figure 4:
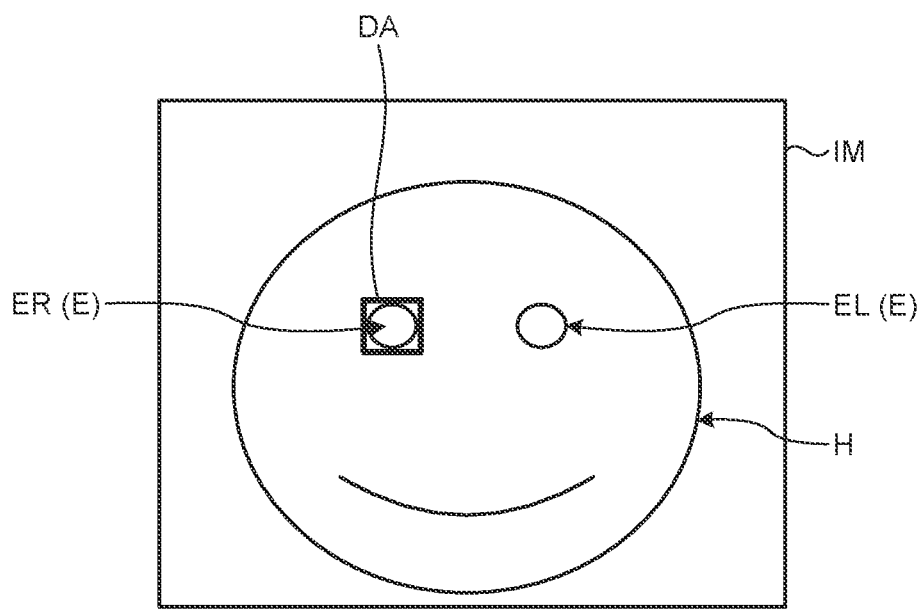
FIG. 4 is a diagram illustrating an example of an operation for detecting eyeball images from a face image.

FIG. 4 is a diagram illustrating an example of the operation for detecting the eyeball images E from the face image IM. As illustrated in FIG. 4, firstly, the eyeball searching unit 33 detects one of the right and left eyeball images E in the obtained face image IM. In the case of detecting only one of the left and right eyeball images E (for example, the right eyeball image ER), the search is performed by setting a search region DA regarding the eyeball image E to be detected. That enables achieving reduction in the processing time as compared to the case in which both of the left and right eyeball images E are detected. When only one of the eyeball images E is detected, the eyeball searching unit 33 searches for the other eyeball image E (for example, the left eyeball image EL) of the subject H from the face image IM based on the search result regarding the already-detected eyeball image E, the subject-device distance D1, and the interocular distance L1.

In that case, the eyeball searching unit 33 calculates the position of the already-detected eyeball image E in the face image IM. Then, the eyeball searching unit 33 predicts the position of the yet-undetected eyeball image based on the eyeball position of the already-detected eyeball image E, the subject-device distance D1, and the interocular distance L1; and performs a search based on the prediction result.

Meanwhile, based on [Expression 3] given earlier, the inter-eyeball-image distance L2 is expressed using [Expression 4] given below.

$$L2 = \frac{F \times 1000 \times L1}{D1 \times P} \quad (4)$$

The eyeball searching unit 33 calculates the inter-eyeball-image distance L2 using [Expression 4] given above. Then, using the inter-eyeball-image distance L2, the eyeball searching unit 33 predicts the eyeball position of the yet-undetected eyeball image E.

That is, first-type search regions are set at the positions separated from the already-detected eyeball image E by the inter-eyeball-image distance L2 in the horizontal direction. Regarding the first-type search regions, coordinates (x, y) of the origins can be expressed as given below in [Expression 5]. Herein, θ represents the angle of the rotation direction around the already-detected eyeball image E.

$$(x, y) = \left( \frac{F \times 1000 \times L2}{D1 \times P} \cos\theta, \frac{F \times 1000 \times L2}{D1 \times P} \sin\theta \right) \quad (5)$$

Figure 5:
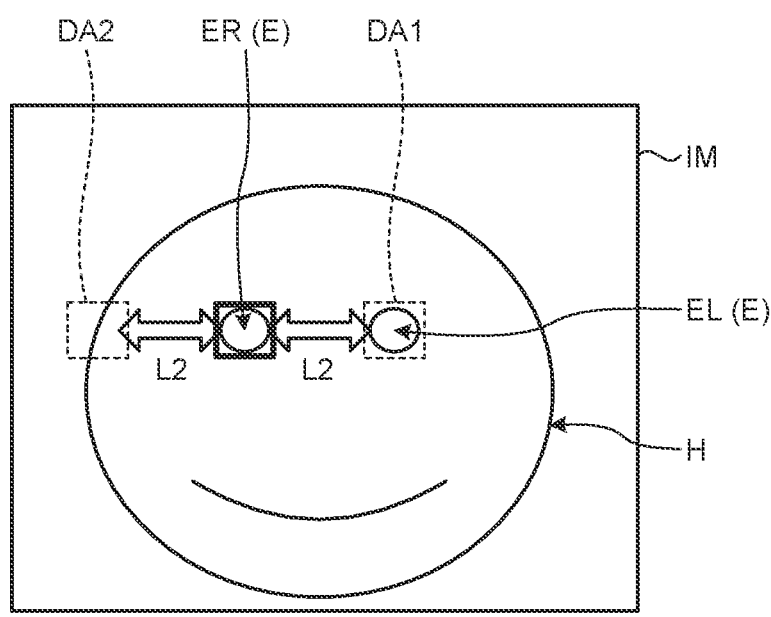
FIG. 5 is a diagram illustrating an example of an operation for predicting the eyeball position of the yet-undetected eyeball image.

FIG. 5 is a diagram illustrating an example of the operation for predicting the eyeball position of the yet-undetected eyeball image E. In the example explained below, the right eyeball image ER represents the already-detected eyeball image, and the left eyeball image EL represents the other eyeball image E that could not be detected. However, that is not the only possible case. That is, for example, the same explanation is applicable to the case in which the left eyeball image EL represents the already-detected eyeball image, and the right eyeball image ER represents the other eyeball image E that could not be detected.

As illustrated in FIG. 5, firstly, the eyeball searching unit 33 sets, with respect to the already-detected right eyeball image ER, first-type search regions DA1 and DA2 at the positions on a virtual straight line M that is parallel to the horizontal direction in the obtained face image IM. The eyeball searching unit 33 sets the first-type search regions DA1 and DA2 in such a way that the distances from the right eyeball image ER to the first-type search regions DA1 and DA2 are equal to the inter-eyeball-image distance L2. Thus, the first-type search regions DA1 and DA2 are set equidistantly from the right eyeball image ER on both sides of the right eyeball image ER in the horizontal direction.

The eyeball searching unit 33 performs a search for the first-type search regions DA1 and DA2. Regarding the first-type search region DA1 present on the right side of the right eyeball image ER and regarding the first-type search region DA2 present on the left side of the right eyeball image ER, the eyeball searching unit 33 can perform a search either simultaneously or at different timings.

Figure 6:
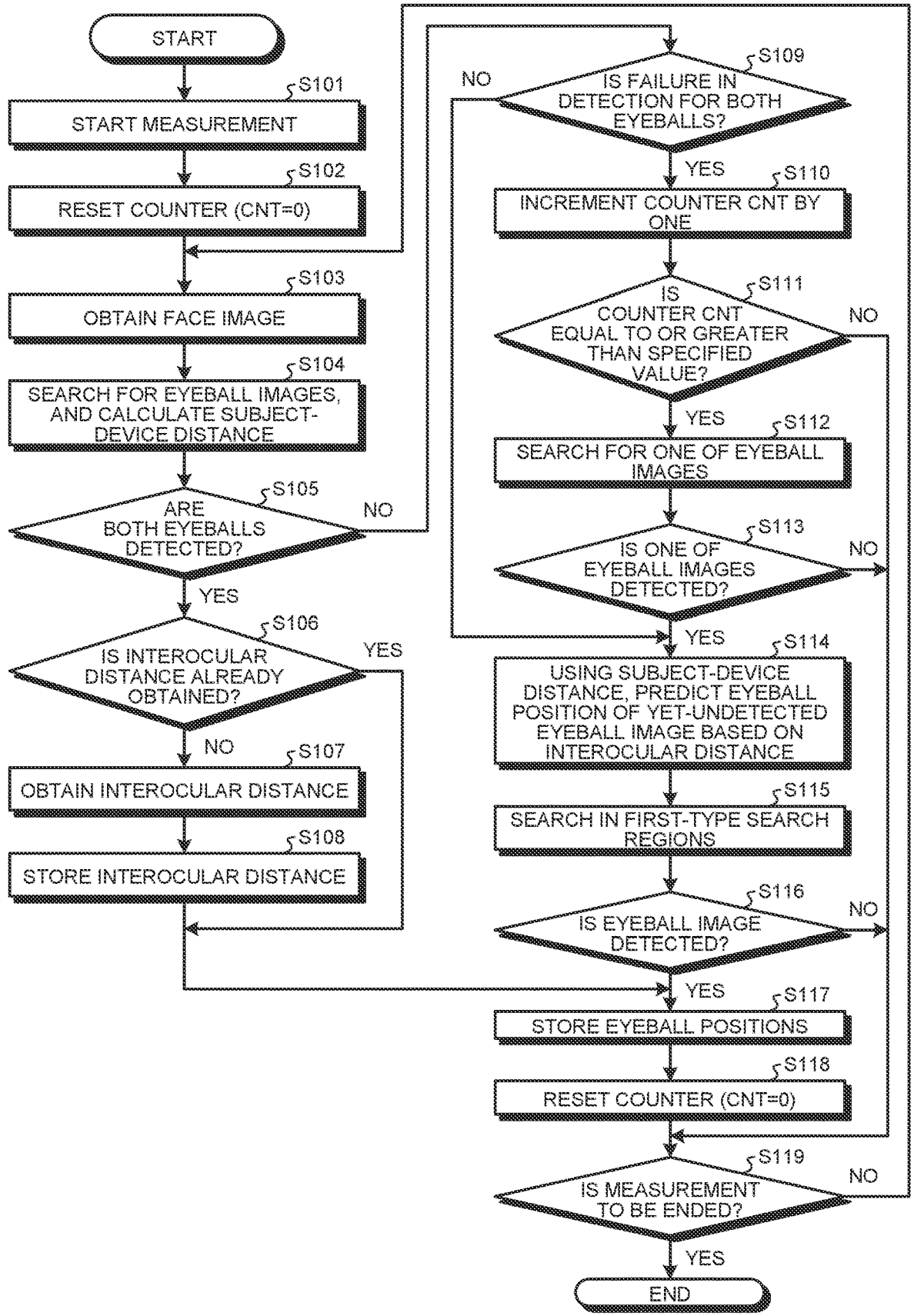
FIG. 6 is a flowchart for explaining an example of an eyeball detection method according to the embodiment.

FIG. 6 is a flowchart for explaining an example of the eyeball detection method according to the present embodiment. As illustrated in FIG. 6, when a measurement start instruction is input (Step S101), the eyeball searching unit 33 resets a counter CNT1 (Step S102) and obtains the face image IM captured by the imaging device 21 (Step S103).

Based on the obtained face image IM, the eyeball searching unit 33 searches for the left and right eyeball images, and the distance calculating unit 32 calculates the subject-device distance D1 (S104). If the eyeball searching unit 33 successfully detects the left and right eyeball images E (Yes at Step S105), then the distance calculating unit 32 determines whether or not the inter-eyeball-image distance L2 is already obtained (Step S106). If it is determined that the inter-eyeball-image distance L2 is not yet obtained (No at Step S106), then the distance calculating unit 32 obtains the inter-eyeball-image distance L2 (Step S107). At Step S107, if the interocular distance L1 of the subject is stored in advance in the memory unit 35, then the distance calculating unit 32 calculates the inter-eyeball-image distance L2 based on the interocular distance L1. However, if the interocular distance L1 is not stored, the distance calculating unit 32 calculates the interocular distance L1 and the inter-eyeball-image distance L2 based on the detection result regarding the eyeball images E. Then, the distance calculating unit 32 stores the inter-eyeball-image distance L2 in the memory unit 35. If the interocular distance L1 of the subject is not stored in advance in the memory unit 35, then the distance calculating unit 32 stores the interocular distance L1 too in the memory unit 35 (Step S108). Then, the system control proceeds to Step S117.

On the other hand, if the eyeball images E are not successfully detected (No at Step S105), then it is determined whether the failure in detection is for both eyeball images E (Step S109). If the failure in detection is for both eyeball images E (Yes at Step S109), then the eyeball searching unit 33 increments the counter CNT1 by one (Step S110), and determines whether or not the value of the counter CNT1 is equal to or greater than a specified value (Step S111). If it is determined that the value of the counter CNT1 is equal to or greater than the specified value (Yes at Step S111), then the eyeball searching unit 33 searches for one of the left and right eyeball images E in the face image (Step S112). If one of the left and right eyeball images E is detected (Yes at Step S113), then the system control proceeds to Step S114.

On the other hand, if it is determined at Step S111 that the value of the counter CNT1 is not equal to or greater than the specified value (No at Step S111) or if no eyeball images E are detected at Step S113 (No at Step S113), then the system control proceeds to Step S119.

When one of the eyeball images E is detected, the eyeball searching unit 33 predicts the eyeball position of the yet-undetected eyeball image E based on the subject-device distance D1 and the inter-eyeball-image distance L2 (Step S114). In the prediction performed at Step S114, the eyeball searching unit 33 sets, with respect to the detected eyeball image E, the first-type search regions DA1 and DA2 at the positions on a virtual straight line that is parallel to the horizontal direction in the obtained face image IM. Then, the eyeball searching unit 33 searches for the yet-undetected eyeball image E in the first-type search regions DA1 and DA2 (Step S115).

If the yet-undetected eyeball image E is detected as a result of performing the search (Yes at Step S116) or after the operation at Step S108 is performed, the eyeball searching unit 33 stores the eyeball positions of the left and right eyeball images E in the memory unit 35 (Step S117), and resets the counter CNT1 (Step S118). On the other hand, if the yet-undetected eyeball image E is not detected (No at Step S116), then the system control proceeds to Step S119.

Subsequently, when a measurement end instruction is input (Step S119), the operations are ended. However, if a measurement end instruction is not input (No at Step S119), then the system control returns to Step S103.

As explained above, the eye-gaze tracking device 100 according to the present embodiment includes: the imaging device 21 that obtains the face IM including the left and right eyeball images E of the subject; the distance calculating unit 32 that calculates the subject-device distance D1 representing the distance between the subject and the imaging device 21; and the eyeball searching unit 33 that searches for the left and right eyeball images E of the subject from the face image IM and, if only one of the left and right eyeball images E of the subject is detected, searches for the yet-undetected eyeball image E of the subject from the face image IM based on the search result for the already-detected eyeball image E, the subject-device distance D1, and the inter-eyeball-image distance L2 representing the distance between the left and right eyeballs of the subject. Moreover, the eye-gaze tracking device 100 according to the present embodiment detects the left and right eyeball images E of the subject, and detects the eye gaze of the subject based on the detection result.

The eyeball detection method according to the present embodiment includes: obtaining the face image IM including the left and right eyeball images E of the subject; calculating the subject-device distance D1 representing the distance between the subject and the imaging device 21; searching for the left and right eyeball images E of the subject from the face image IM; and, if only one of the left and right eyeball images E of the subject is detected, searching for the yet-undetected eyeball image E of the subject from the face image IM based on the search result for the already-detected eyeball image E, the subject-device distance D1, and the inter-eyeball-image distance L2 representing the distance between the left and right eyeballs of the subject.

The eyeball detection program according to the present embodiment causes a computer to perform: an operation of obtaining the face image IM including the left and right eyeball images E of the subject; an operation of calculating the subject-device distance D1 representing the distance between the subject and the imaging device 21; an operation of searching for the left and right eyeball images E of the subject from the face image IM; and, if only one of the left and right eyeball images E of the subject is detected, an operation of searching for the yet-undetected eyeball image E of the subject from the face image IM based on the search result for the already-detected eyeball image E, the subject-device distance D1, and the inter-eyeball-image distance L2 representing the distance between the left and right eyeballs of the subject.

In the present embodiment, when only one of the left and right eyeball images E of the subject is detected, the other eyeball image E of the subject is searched from the face image IM based on the search result for the already-detected eyeball image E, the subject-device distance D1, and the inter-eyeball-image distance L2 representing the distance between the left and right eyeballs of the subject. That enables achieving shortening of the processing time as compared to the case of detecting both of the left and right eyeball images E. Hence, it becomes possible to shorten the processing time when detecting the eyeballs of the subject.

In the eye-gaze tracking device 100 according to the present embodiment, the eyeball searching unit 33 calculates the eyeball position of one of the eyeball images E based on that eyeball image E; predicts the eyeball position of the other eyeball image E based on the eyeball position of the former eyeball image E, the subject-device distance D1, and the inter-eyeball-image distance L2; and performs a search based on the prediction result. That results in an enhancement in the search accuracy of the other eyeball image E.

In the eye-gaze tracking device 100 according to the present embodiment, the distance calculating unit 32 calculates the inter-eyeball-image distance L2 based on the face image IM obtained by the imaging device 21. As a result, even if the inter-ocular distance L1 of the subject is not obtained in advance, the inter-eyeball-image distance L2 can still be obtained.

In the eye-gaze tracking device 100 according to the present embodiment, the distance calculating unit 32 calculates the subject-device distance D1 based on the face image obtained by the imaging device 21. That eliminates the need to separately provide a unit for measuring the subject-device distance D1, thereby making it possible to calculate the subject-device distance D1 in an efficient manner.

Meanwhile, the technical scope of the present disclosure is not limited to the embodiment described above, and can be construed as embodying various deletions, alternative constructions, and modifications that may occur to one skilled in the art that fairly fall within the basic teaching herein set forth. For example, in the embodiment described above, when the yet-undetected eyeball image E is not detected in the first-type search regions DA1 and DA2 (see FIG. 5), the eyeball searching unit 33 can set second-type search regions that are shifted by a predetermined angle with respect to the first-type search regions DA1 and DA2 in the rotation direction around the eyeball position of the already-detected eyeball image E; and can perform a search in the second-type search regions.

Figure 7:
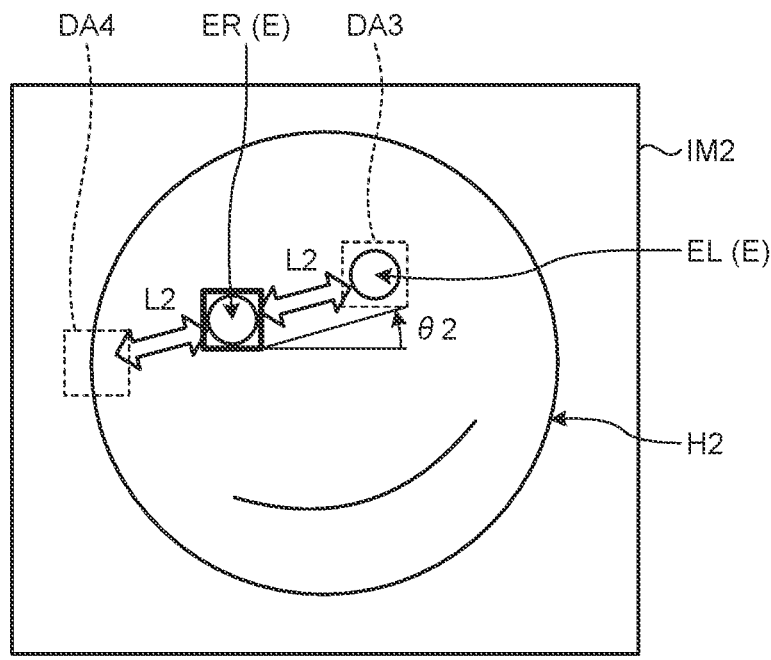
FIG. 7 is a diagram illustrating another example of the operation for predicting the eyeball position of the yet-undetected eyeball image.
Figure 8:
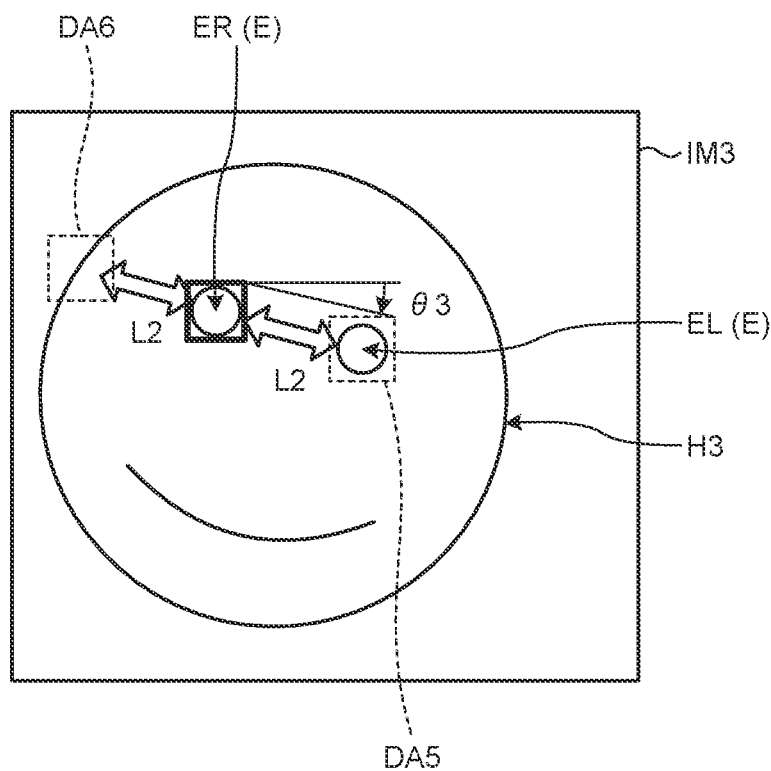
FIG. 8 is a diagram illustrating still another example of the operation for predicting the eyeball position of the yet-undetected eyeball image.

FIGS. 7 and 8 are diagrams illustrating another example of the operation for predicting the eyeball position of the yet-undetected eyeball image E. As illustrated in FIG. 7, the eyeball searching unit 33 sets second-type search regions DA3 and DA4 at the positions shifted by an angle θ2 with respect to the first-type search regions DA1 and DA2 in the counterclockwise direction around the right eyeball image ER of a subject H2; and performs a search in the second-type search regions DA3 and DA4. In that case, the distances from the right eyeball image ER to the second-type search regions DA3 and DA4 are equal to the inter-eyeball-image distance L2.

If the yet-undetected eyeball image E is still not found in the second-type search regions DA3 and DA4 illustrated in FIG. 7, then the eyeball searching unit 33 sets second-type search regions at the positions further shifted by the angle θ2 with respect to the second-type search regions DA3 and DA4 in the counterclockwise direction around the right eyeball image ER; and performs a search in the newly-set second-type search regions. Thereafter, every time the yet-undetected eyeball image E is not found in the newly-set second-type search regions, the eyeball searching unit 33 sets second-type search regions at the positions further shifted by the angle θ2 with respect to the existing second-type search regions in the counterclockwise direction around the right eyeball image ER; and performs a search in the newly-set second-type search regions. The eyeball searching unit 33 can set the second-type search regions within the range of angles up to a predetermined angle with respect to the first-type search regions DA1 and DA2 in the counterclockwise direction around the right eyeball image ER.

Meanwhile, if the yet-undetected eyeball image E is not found even after performing a search by setting the second-type search regions within a predetermined range of angles with respect to the first-type search regions DA1 and DA2 in the counterclockwise direction around the right eyeball image ER; then, as illustrated in FIG. 8, the eyeball searching unit 33 sets second-type search regions DA5 and DA6 at the positions shifted by an angle θ3 with respect to the first-type search regions DA1 and DA2 in the clockwise direction around the right eyeball image ER; and performs a search in the second-type search regions DA5 and DA6. In that case, the distances from the right eyeball image ER to the second-type search regions DA5 and DA6 are equal to the inter-eyeball-image distance L2.

If the yet-undetected eyeball image E of the subject H3 is not found in the second-type search regions DA5 and DA6 illustrated in FIG. 8, then the eyeball searching unit 33 sets second-type search regions at the positions further shifted by the angle θ3 with respect to the second-type search regions DA5 and DA6 in the counterclockwise direction around the right eyeball image ER; and performs a search in the newly-set second-type search regions. Thereafter, every time the yet-undetected eyeball image E is not found in the newly-set second-type search regions, the eyeball searching unit 33 sets second-type search regions at the positions further shifted by the angle θ3 with respect to the existing second-type search regions in the counterclockwise direction around the right eyeball image ER; and performs a search in the newly-set second-type search regions. The eyeball searching unit 33 can set the second-type search regions within the range of angles up to a predetermined angle with respect to the first-type search regions DA1 and DA2 in the clockwise direction around the right eyeball image ER. Meanwhile, with reference to FIGS. 7 and 8, the explanation is given for the example in which the second-type search regions are firstly set in the counterclockwise direction and are then set in the clockwise direction. However, that is not the only possible case. That is, in the opposite manner, the second-type search regions can be firstly set in the clockwise direction and can then be set in the counterclockwise direction.

FIG. 9 is a flowchart for explaining the eyeball detection method according to a modification example. As illustrated in FIG. 9, other than Step S116, all other steps are identical to the embodiment described above. As a result of the determination performed at Step S116, if it is determined that the yet-undetected eyeball image E is detected in the first-type search regions DA1 and DA2 (Yes at Step S116), then the operations from Step S117 are performed in an identical manner to the embodiment described above.

On the other hand, if it is determined that the yet-undetected eyeball image E is not detected in the first-type search regions DA1 and DA2 (No at Step S116), then the eyeball searching unit 33 sets second-type search regions within the range of angles up to a predetermined angle with respect to the first-type search regions DA1 and DA2 either in the counterclockwise direction or in the clockwise direction around the right eyeball image ER (Step S120). At Step S120, if the second-type search regions are moved by an angle equal to or greater than a predetermined angle with respect to the first-type search regions (Step S121), then the operations from Step S119 are performed. Moreover, at Step S120, if the second-type search regions are moved by an angle smaller than the predetermined angle with respect to the first-type search regions (Step S121), then the operations from Step S119 onward are performed.

In this way, if the yet-undetected eyeball image E is not detected in the first-type search regions DA1 and DA2, then the eyeball searching unit 33 sets second-type search regions at a predetermined angle with respect to the first-type search regions DA1 and DA2 in the rotation direction around the already-detected eyeball image E; and performs a search in the second-type search regions. As a result, also in the case in which the yet-undetected eyeball image E is shifted with respect to the already-detected eyeball image E in the rotation direction, such as in the case in which the face of the subject is inclined; it becomes possible to detect the yet-undetected eyeball image E. That enables achieving enhancement in the detection accuracy of the eyeball images E.

Meanwhile, in the embodiment described above, the explanation is given about the configuration in which the eyeball detection device is implemented in the eye-gaze tracking device 100. However, that is not the only possible case. Alternatively, for example, the eyeball detection device can be implemented in some other device such as a face image recognition device in which the face image of the target person is obtained and the eyeball images are detected from the face image.

Moreover, in the embodiment described above, the explanation is given about the example in which the subject-device distance D1 is calculated from the first camera 21A and the second camera 21B of the imaging device 21. However, that is not the only possible case. Alternatively, the distance can be measured using, for example, a laser ranger.

INDUSTRIAL APPLICABILITY

An eyeball detection device, an eye-gaze tracking device, an eyeball detection method, and an eyeball detection program according to the present disclosure can be implemented in, for example, an eye-gaze tracking device.

According to the present disclosure, it becomes possible to provide an eyeball detection device, an eye-gaze tracking device, an eyeball detection method, and an eyeball detection program that enable shortening of the processing time at the time of detecting the eyeballs of the target person.

What is claimed is:

1. An eyeball detection device comprising:
an imaging device that obtains a face image which includes left and right eyeball images of target person;
a first distance calculating unit that calculates a first-type distance representing distance between the target person and the imaging device; and
an eyeball searching unit that performs a search for the left and right eyeball images from the face image and, when one eyeball image of the left and right eyeball images of the target person is detected, searches for other eyeball image of the target person from the face image based on search result regarding the one eyeball image as obtained by the eyeball detecting unit, based on the first-type distance, and based on a second-type distance representing distance between left and right eyeballs of the target person,
wherein the eyeball searching unit calculates eyeball position based on the one eyeball image of the left and right eyeball images,
predicts eyeball position of the other eyeball image based on eyeball position of the one eyeball image, based on the first-type distance, and based on the second-type distance,
performs the search based on prediction results,
sets, with respect to the one eyeball image, first-type search regions at positions on a vertical straight line that is parallel to a horizontal direction, and performs the search in the first-type search regions, and
when the other eyeball image is not detected in the first-type search regions, sets second-type search regions that are shifted by a predetermined angle with respect to the first-type search regions in a rotation direction around a position of the one image, and performs the search in the second-type search regions.

2. The eyeball detection device according to claim 1, further comprising a second distance calculating unit that calculates the second-type distance based on the face image obtained by the imaging device.

3. The eyeball detection device according to claim 1, wherein the first distance calculating unit calculates the first-type distance based on the face image obtained by the imaging device.

4. An eye-gaze tracking device that
detects left and right eyeball images of target person using the eyeball detection device according to claim 1, and
tracks eye gaze of the target person based on detection result.

5. An eyeball detection method comprising:
obtaining a face image that includes left and right eyeball images of target person;
calculating a first-type distance representing distance between the target person and the imaging device;
performing a search for the left and right eyeball images from the face image; and
searching that, when one eyeball image of the left and right eyeball images of the target person is detected, includes searching for other eyeball image of the target person from the face image based on search result regarding the one eyeball image, based on the first-type distance, and based on a second-type distance representing distance between left and right eyeballs of the target person, wherein the searching calculates eyeball position based on the one eyeball image of the left and right eyeball images, predicts eyeball position of the other eyeball image based on eyeball position of the one eyeball image, based on the first-type distance, and based on the second-type distance, performs the search based on prediction results, sets, with respect to the one eyeball image, first-type search regions at positions on a vertical straight line that is parallel to a horizontal direction, and performs the search in the first-type search regions, and when the other eyeball image is not detected in the first-type search regions, sets second-type search regions that are shifted by a predetermined angle with respect to the first-type search regions in a rotation direction around a position of the one image, and performs the search in the second-type search regions.

6. A non-transitory computer readable recording medium storing therein an eyeball detection program that causes a computer to execute:

an operation of obtaining a face image that includes left and right eyeball images of target person;

an operation of calculating a first-type distance representing distance between the target person and the imaging device;

an operation of performing a search for the left and right eyeball images from the face image; and an operation of searching that, when one eyeball image of the left and right eyeball images of the target person is detected, includes searching for other eyeball image of the target person from the face image based on search result regarding the one eyeball image, based on the first-type distance, and based on a second-type distance representing distance between left and right eyeballs of the target person, wherein the operation of searching calculates eyeball position based on the one eyeball image of the left and right eyeball images, predicts eyeball position of the other eyeball image based on eyeball position of the one eyeball image, based on the first-type distance, and based on the second-type distance, performs the search based on prediction results, sets, with respect to the one eyeball image, first-type search regions at positions on a vertical straight line that is parallel to a horizontal direction, and performs the search in the first-type search regions, and when the other eyeball image is not detected in the first-type search regions, sets second-type search regions that are shifted by a predetermined angle with respect to the first-type search regions in a rotation direction around a position of the one image, and performs the search in the second-type search regions.

* * * * *